United States Patent
Chen et al.

(10) Patent No.: US 12,048,840 B2
(45) Date of Patent: Jul. 30, 2024

(54) SAFETY INJECTION DEVICE, INJECTOR AND ASSEMBLY METHOD THEREOF

(71) Applicant: NINGBO MEDSUN MEDICAL CO., LTD., Zhejiang (CN)

(72) Inventors: Zhicheng Chen, Zhejiang (CN); Fengxia Wu, Zhejiang (CN)

(73) Assignee: NINGBO MEDSUN MEDICAL CO., LTD., Ningbo (CN)

(*) Notice: Subject to any disclaimer, the term of this patent is extended or adjusted under 35 U.S.C. 154(b) by 632 days.

(21) Appl. No.: 17/303,847

(22) Filed: Jun. 9, 2021

(65) Prior Publication Data

US 2021/0290858 A1  Sep. 23, 2021

Related U.S. Application Data

(63) Continuation of application No. PCT/CN2019/093149, filed on Jun. 27, 2019.

(30) Foreign Application Priority Data

Dec. 27, 2018 (CN) .......................... 201811614986.6
Apr. 2, 2019 (CN) .......................... 201910260356.1

(51) Int. Cl.
*A61M 5/32* (2006.01)
*A61M 5/50* (2006.01)

(52) U.S. Cl.
CPC ........ *A61M 5/3245* (2013.01); *A61M 5/3213* (2013.01); *A61M 5/3271* (2013.01); *A61M 5/5086* (2013.01); *A61M 2005/3267* (2013.01); *A61M 2207/00* (2013.01)

(58) Field of Classification Search
CPC ........ A61B 5/150618; A61B 5/150916; A61B 5/15144; A61M 5/3271; A61M 5/3245
See application file for complete search history.

(56) References Cited

U.S. PATENT DOCUMENTS

| 7,001,364 B1 | 2/2006 | Farhi |
| 2002/0004648 A1 | 1/2002 | Larsen et al. |
| 2016/0331905 A1 | 11/2016 | Aneas |

FOREIGN PATENT DOCUMENTS

| CN | 1596138 A | 3/2005 |
| CN | 101563125 A | 10/2009 |
| CN | 102905747 A | 1/2013 |
| CN | 104771815 A | 7/2015 |
| CN | 206325077 U | 7/2017 |
| CN | 107106775 A | 8/2017 |
| CN | 206660239 U | 11/2017 |

(Continued)

*Primary Examiner* — Deanna K Hall

(57) ABSTRACT

The present application discloses a safety injection device including a needle, a needle hub, an elastic member, a slider, a needle shield, a protective sleeve, and an outer cover. The needle hub, the elastic member, the slider, the needle shield and the protective sleeve are sleeved in sequence with the needle as a shaft. The slider is configured to rotate irreversibly after a single use. The safety injection device according to the present application has a simple and reasonable structure, and is safe, stretchable, and easy to use. In addition, it avoids fear of the needle tip during injection when use. After use, the injection device utilizes the eccentric principle to prevent from being fully depressed again, and the needle tip will not be exposed again, thereby more effectively avoiding the risk of cross infection caused by accidental contact with the needle tip after use.

14 Claims, 15 Drawing Sheets

(56) References Cited

FOREIGN PATENT DOCUMENTS

| | | |
|---|---|---|
| CN | 107750175 A | 3/2018 |
| CN | 107823761 A | 3/2018 |
| CN | 207822207 U | 9/2018 |
| CN | 109847151 A | 6/2019 |
| EP | 2090326 A1 | 8/2009 |
| JP | 2018198932 A | 12/2018 |
| WO | 03045480 A1 | 6/2003 |
| WO | 2011117283 A2 | 9/2011 |

SAFETY INJECTION DEVICE, INJECTOR AND ASSEMBLY METHOD THEREOF

CROSS-REFERENCE TO RELATED APPLICATIONS

The present application is a continuation application of PCT application No. PCT/CN2019/093149, filed on Jun. 27, 2019, which is hereby incorporated by reference in its entirety.

TECHNICAL FIELD

The present application relates to a field of medical instruments, and in particular, to a safety injection device, an injector, and an assembly method thereof.

BACKGROUND

Insulin injection devices such as insulin pens and injection needles have been widely used as a method of treating diabetes, the main function of which is to precisely inject insulin into the body of a diabetic patient through an injection device, so as to achieve the purpose of controlling the blood glucose of the patient. With the increasing number of diabetic patients, the demand for insulin injection devices is increasing.

A traditional injection needle includes a needle hub, a needle, and an outer protective sleeve. After removing the protective sleeve before use, the insulin injection needle is directly exposed to the outside. Due to lack of protective structure after use, cross infection caused by accidental contact with the needle is prone to occur, and the used needle may be reused, resulting a very high risk of infection.

Some safety insulin needles in the prior art that solve the problems of traditional injection needles mentioned above have the following disadvantages:

i. The safety insulin needle cannot protect the needle tip immediately after the injection is completed. Instead, the protective structure can only protect the needle tip after the injection device such as the insulin pen is withdrawn, thus there is still a risk of cross infection due to accidental touch.

ii. Insulin is usually injected into the subcutaneous tissue layer rather than the muscle layer, since insulin is absorbed quickly in the muscle layer, which can easily cause blood glucose fluctuations. When the needle is too long or the patient's subcutaneous tissue layer is too thin, it not only increases the difficulty of operation, but also makes the injection risky and even cannot be completed.

iii. Also due to the existence of structures such as needle shield, the needle resistance during injection is relatively large, which makes the patient experience worse and increases the difficulty of operation.

iv. Many existing insulin needles in the market have complicated structures, high manufacturing and use costs, which bring economic burden to diabetic patients.

SUMMARY

In view of the above-mentioned shortcomings of the prior art, the technical problem to be solved by the present application is how to ensure that the injection device can be used only once from the aspect of mechanical structure, and cannot be reused.

To achieve the above object, the present application provides a safety injection device, wherein the injection device includes at least:

a needle, with one end connecting to an injection as a proximal end and the other end as a distal end;

a slider, being sleeved on the needle with the needle as a shaft;

a needle shield, being sleeved on the needle with the needle as a shaft, and a proximal end of the needle shield being in contact with a distal end of the slider;

a protective sleeve, being sleeved on the needle with the needle as a shaft, and an inner wall of the protective sleeve being in contact with an outer wall of the needle shield and an outer wall of the slider;

an elastic member, being sleeved on the needle with the needle as a shaft, and a distal end of the elastic member being in contact with a proximal end of the slider;

wherein, the slider is configured to rotate irreversibly after a single use.

Further, the proximal end surface of the needle shield has a first inclined surface; the slider has a pressure receiving portion being in contact with the first inclined surface of the needle shield; and when the needle shield moves toward the slider, the pressure receiving portion moves along the first inclined surface.

Further, one end of the first inclined surface has a blocking portion, and when the pressure receiving portion comes into contact with the blocking portion, the slider stops rotating and the elastic member is compressed.

Further, a guide structure is provided on the inner wall of the protective sleeve, the guide structure includes a guide block, the guide block has a third inclined surface; the outer wall of the slider has a limiting protrusion, and the limiting protrusion is in contact with the third inclined surface; when the needle shield continues to move toward the slider, the elastic member continues to compress, the limiting protrusion moves under the guidance of the third inclined surface, the pressure receiving portion crosses the blocking portion and disengages from the first inclined surface, the slider continues to rotate, and the pressure receiving portion falls into the restricting area of the needle shield.

Further, the guide structure further includes a guide bar, the outer wall of the proximal end of the needle shield has a groove, and the groove cooperates with the guide bar to prevent relative rotation between the needle shield and the protective sleeve with the needle as a shaft.

Further, the slider cannot return to an initial position after the elastic force of the elastic member is completely released since the pressure receiving portion falls into the restricting area of the needle shield.

Further, the injection device further includes a needle hub which is sleeved on the needle with the needle as a shaft, and a proximal end the needle hub is in contact with the proximal end of the protective sleeve; the needle hub includes a base and a rod, and the rod includes a rod core and an extension portion; wherein the proximal end of the slider has a through hole; when the pressure receiving portion enters the restricting area of the needle shield, the shapes of the extension portion and the through hole do not match and interfere, the movement of the needle shield towards the slider no longer causes deformation of the elastic member.

Further, the distal end of the needle shield is provided with a first hole, through which the distal end of the needle protrudes from the needle shield to contact an injection site.

Further, the distal end of the protective sleeve is provided with a second hole and the needle shield passes through the second hole for axial reciprocating motion with the needle as a shaft.

Further, the outside wall of the protective sleeve is provided with a reinforcing rib with an inclined surface and the reinforcing rib extends to the proximal end of the protective sleeve.

Further, the cross-sectional shape of the extension portion is rectangular or oval.

Further, an outside wall of the proximal end of the needle hub is provided with a lug or threads or concave-convex teeth, and an outside wall of the proximal end of the protective sleeve is correspondingly provided with a groove or threads or concave-convex teeth.

Further, the slider has a different color from other components, and the needle shield sleeved outside the slider is made of transparent material.

The application also provides an injector comprising the safety injection device as described above.

The application also provides a method for assembling a safety injection device, which includes at least the following steps:
1) inserting a needle into a needle hub;
2) sleeving an elastic member, a slider, a needle shield and a protective sleeve sequentially with the needle as a shaft.

The safety injection device of the present application has a simple and reasonable structure, and is safe, stretchable, and easy to use. In addition, it avoids fear of the needle tip during injection when use. The injection device has a reasonable and safe path (i.e. effective injection through the stretching and contracting of the spring during use). After use, the device utilizes the eccentric principle to prevent from being fully depressed again, and the needle tip will not be exposed again. It avoids reuse and cross infection, and can immediately protect the needle, thereby more effectively avoiding the risk of cross infection caused by accidental contact with the needle tip after use. This structure makes it difficult to return to the initial position to be used after use, so that the injection needle is safer after use and will not be used again, which effectively avoids cross infection. The safety injection device is not only convenient for patients, but also safer and more reliable. After use, the injection device utilizes its colored and raised slider as a warning indicating that it has been used.

The concept, specific structure, and technical effects of the present application will be further described below with reference to the accompanying drawings to fully understand the objects, features, and effects of the present application.

Figure 1:
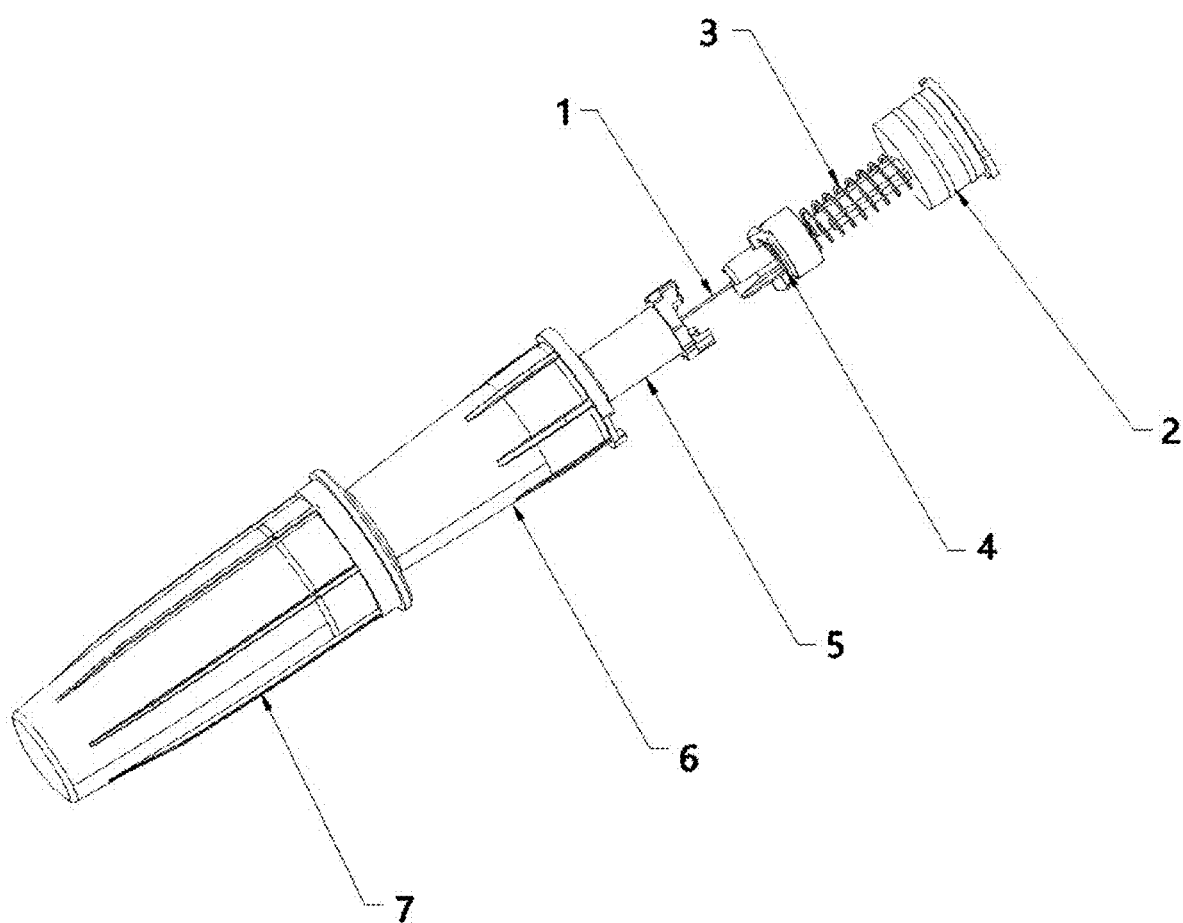
FIG. 1 is a schematic diagram of connection and assembly of an injection device according to a preferred embodiment of the present application.

In the FIGS.: 1. needle; 11. proximal end of needle; 12. distal end of needle; 2. needle hub; 21. base; 211. lug; 22. rod; 221. rod core; 222. extension portion; 3. spring; 4. slider; 41. guide portion; 411. through groove; 42. pressure receiving portion; 421. second inclined surface; 422. limiting protrusion; 5. needle shield; 51. distal end surface of needle shield; 511. first hole; 52. proximal end surface of needle shield; 521. first inclined surface; 522. restricting area; 523. blocking portion; 6. protective sleeve; 61. distal end surface of protective sleeve; 611. second hole; 62. proximal end surface of protective sleeve; 621. snap ring; 622. notch; 63. reinforcing rib; and 7. outer cover.

DETAILED DESCRIPTION

The following describes the preferred embodiments of the present application with reference to the accompanying drawings to make the technical content clearer and easier to understand. The present application may be embodied in many different forms of embodiments, and the protection scope of the present application is not limited to the embodiments mentioned herein.

In the drawings, components having the same structure are denoted by the same numerals, and components having similar structures or functions are denoted by similar numerals. The size and thickness of each component shown in the drawings are arbitrarily shown, and the present application does not limit the size and thickness of each component. In order to make the illustration clearer, the thickness of component is exaggerated in some places in the drawings.

As shown in FIG. 1, the safety injection device according to the present application includes a needle 1, a needle hub 2, a spring 3, a slider 4, a needle shield 5, a protective sleeve 6, and a outer cover 7. The part where the needle 1 and the needle hut 2 are connected is the proximal end 11 of the needle 1 and the other end is the distal end 12 of the needle 1. A needle hub 2, a spring 3, a slider 4, a needle shield 5, a protective sleeve 6 and an outer cover 7 are sleeved along the direction from the proximal end 11 to the distal end 12 of the needle 1 in sequence.

Figure 2:
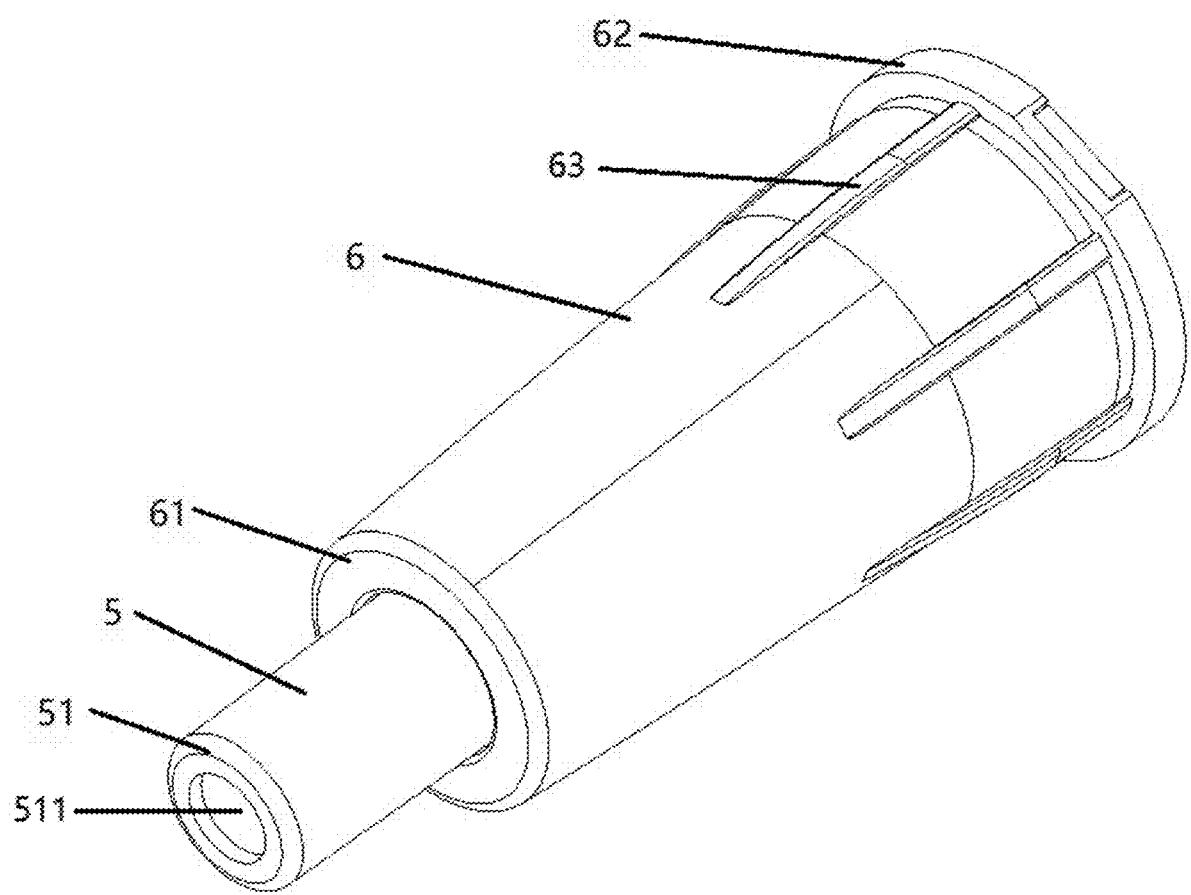
FIG. 2 is a schematic diagram of the appearance of a needle shield and a protective sleeve according to a preferred embodiment of the present application.

As shown in FIG. 2, the needle shield 5 has a distal end surface 51, and the distal end surface 51 is provided with a first hole 511. The first hole 511 is used for extending the distal end of the needle 1 to contact the injection site. The distal end surface 61 of the protective sleeve 6 is provided with a second hole 611. The needle shield 5 penetrates the second hole 611 to perform an axial reciprocating motion with the needle 1 as a shaft. The outer wall of the protective sleeve 6 is provided with a reinforcing rib 63 having an inclined surface. The reinforcing rib 63 extends to the proximal end surface 62 of the protective sleeve 6. The reinforcing rib 63 has an inclined surface for connecting and fixing the outer cover 7.

Figure 3:
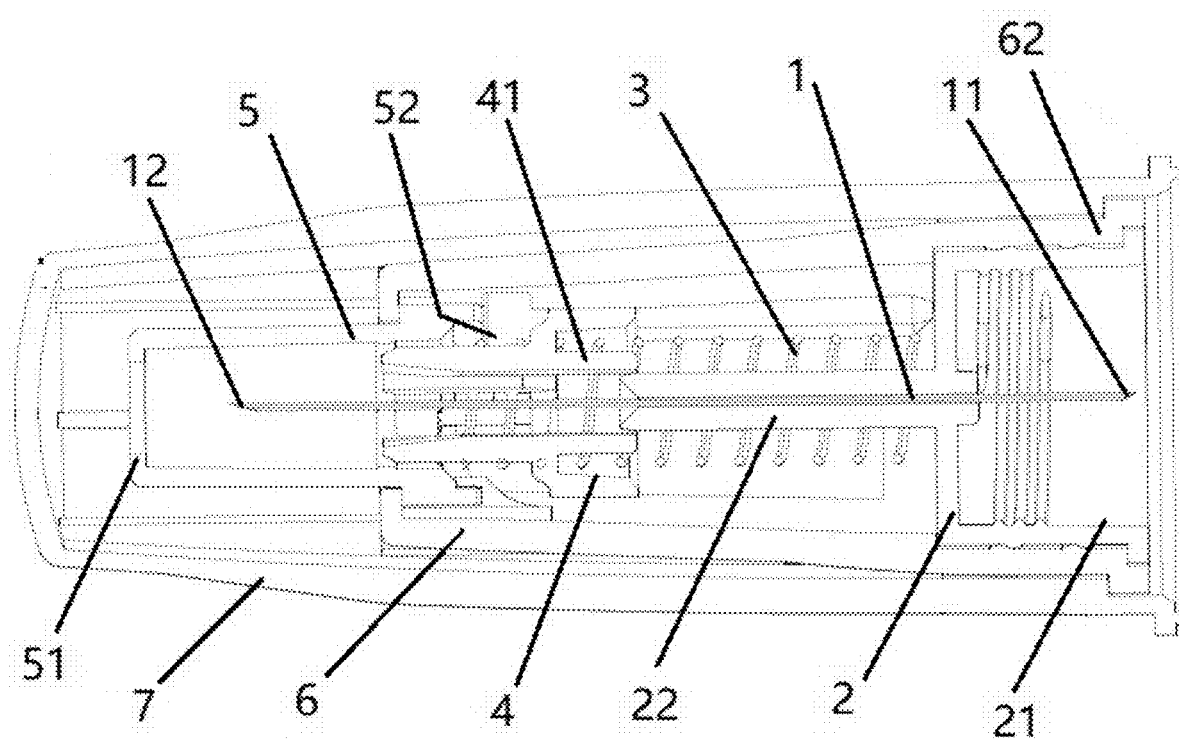
FIG. 3 is a sectional view of an injection device in an unused state according to a preferred embodiment of the present application.
Figure 4:
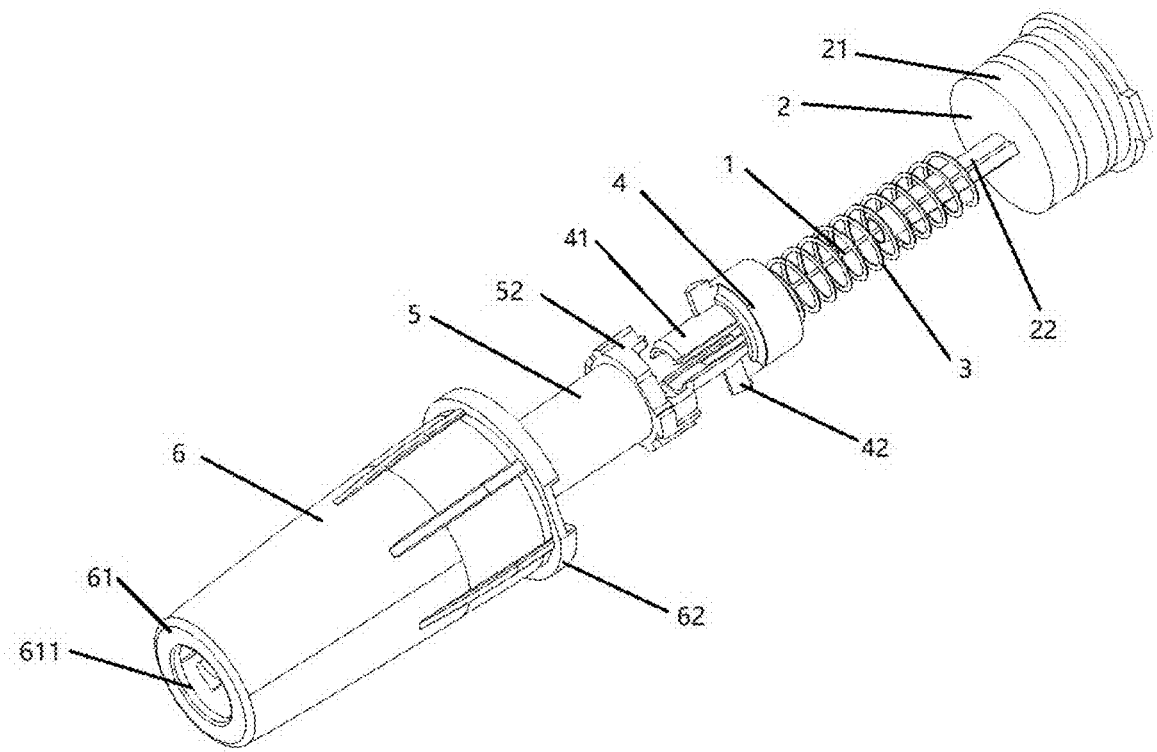
FIG. 4 is a schematic diagram of connection and assembly of an injection device according to a preferred embodiment of the present application.

FIG. 3 is a sectional view of the safety injection device in an unused state. FIG. 4 is an exploded view of the safety injection device without the outer cover 7. A protective sleeve 6 is provided outside the needle shield 5. The distal end surface 51 of the needle shield 5 penetrates through the second hole 611 of the protective sleeve 6. The proximal end surface 52 of the needle shield 5 is in contact with the pressure receiving portion 42 of the slider 4. The slider 4 has a guide portion 41, the distal end of the guide portion 41 is fitted into the inside of the needle shield 5, and the proximal end of the guide portion 41 is fitted into the distal end of the spring 3. The pressure receiving portion 42 has an inclined surface and is provided outside the guide portion 41. The proximal end of the spring 3 is sleeved on the rod 22 of the needle hub 2.

Figure 5:
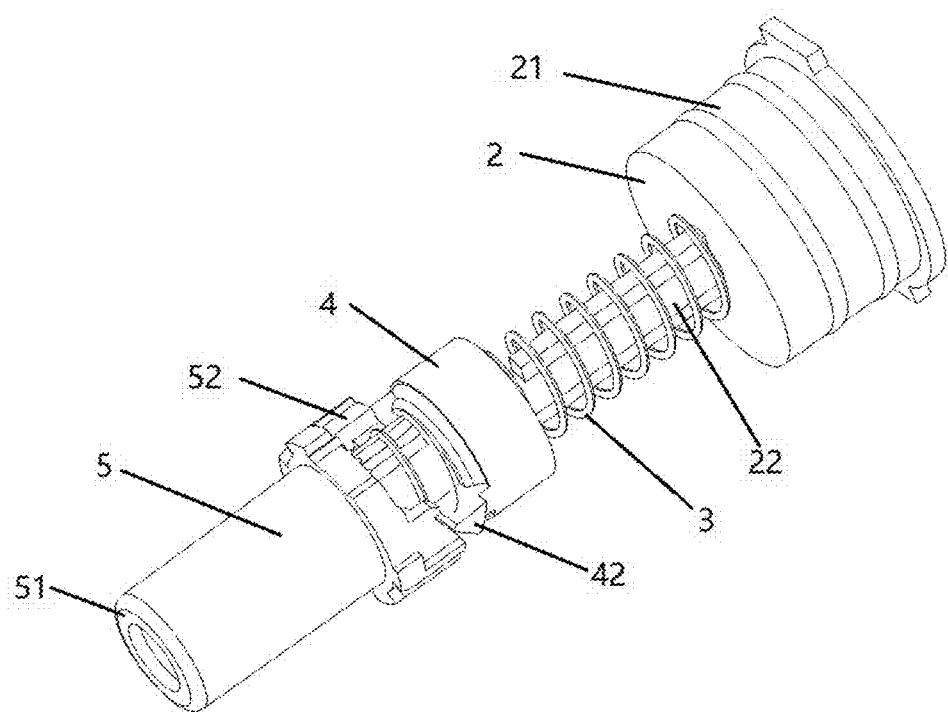
FIG. 5 is a perspective view a needle shield, a slider, a spring, and a needle hub in working state according to a preferred embodiment of the present application.
Figure 6:
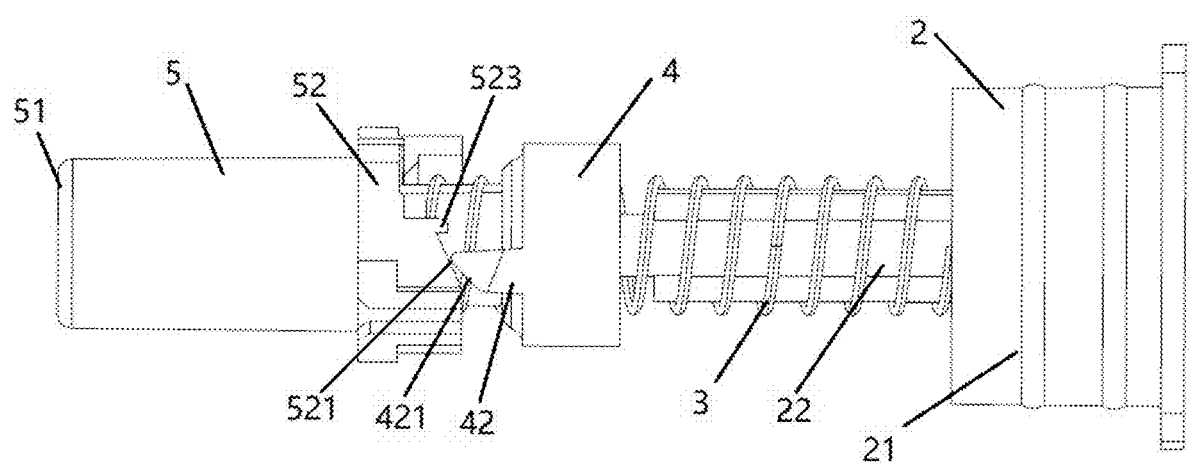
FIG. 6 is a side view of a needle shield, a slider, a spring, and a needle hub in working state according to a preferred embodiment of the present application.

As shown in FIGS. 5 and 6, when the distal end surface 51 of the needle shield 5 is pressed, the pressure is transmitted to the spring 3 through the slider 4, causing the spring 3 to compress and deform. The spring 3 generates a counterforce against the slider 4 such that the slider 4 is in close contact with the needle shield 5, the slider 4 rotates under the limitation of the guide portion 41 with the needle 1 as a shaft, and the slider 4 is locked at the blocking portion 523 at one end of the first inclined surface 521. At the same time, the slider 4 no longer rotates until the spring 3 reaches the maximum deformation. In this way, the distal end of the needle 1 extends beyond the distal end of the needle shield 5 and is in an injection state. After the injection is completed, the spring 3 starts to recover from the deformation when the compression applied to the distal surface 51 of the needle shield 5 is removed.

Figure 7:
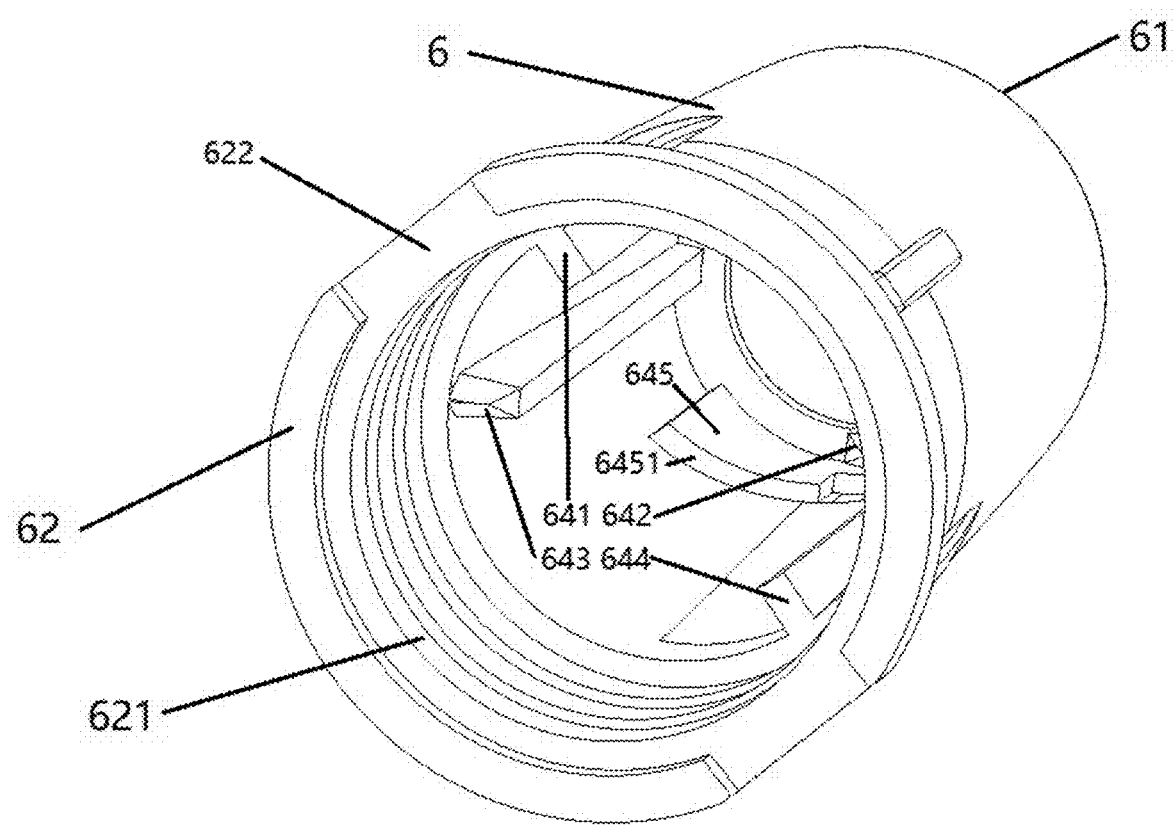
FIG. 7 is a schematic diagram of the internal structure of a protective sleeve according to a preferred embodiment of the present application.
Figure 20:
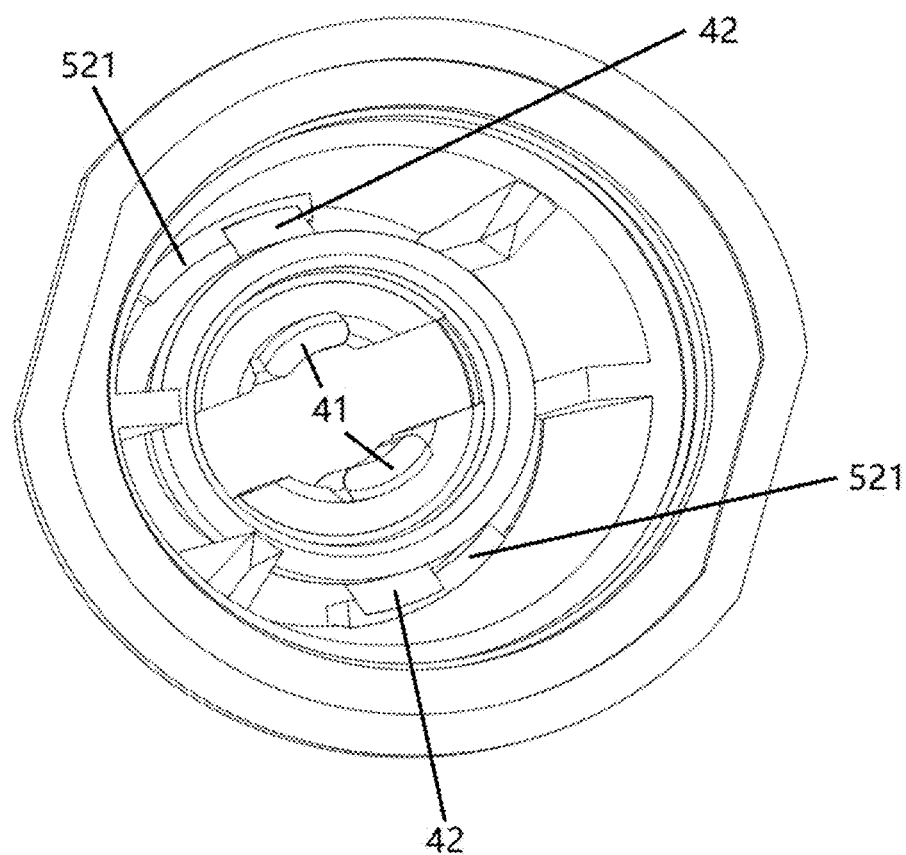
FIG. 20 is a schematic diagram of cooperation between a slider and a protective sleeve according to a preferred embodiment of the present application.
Figure 21:
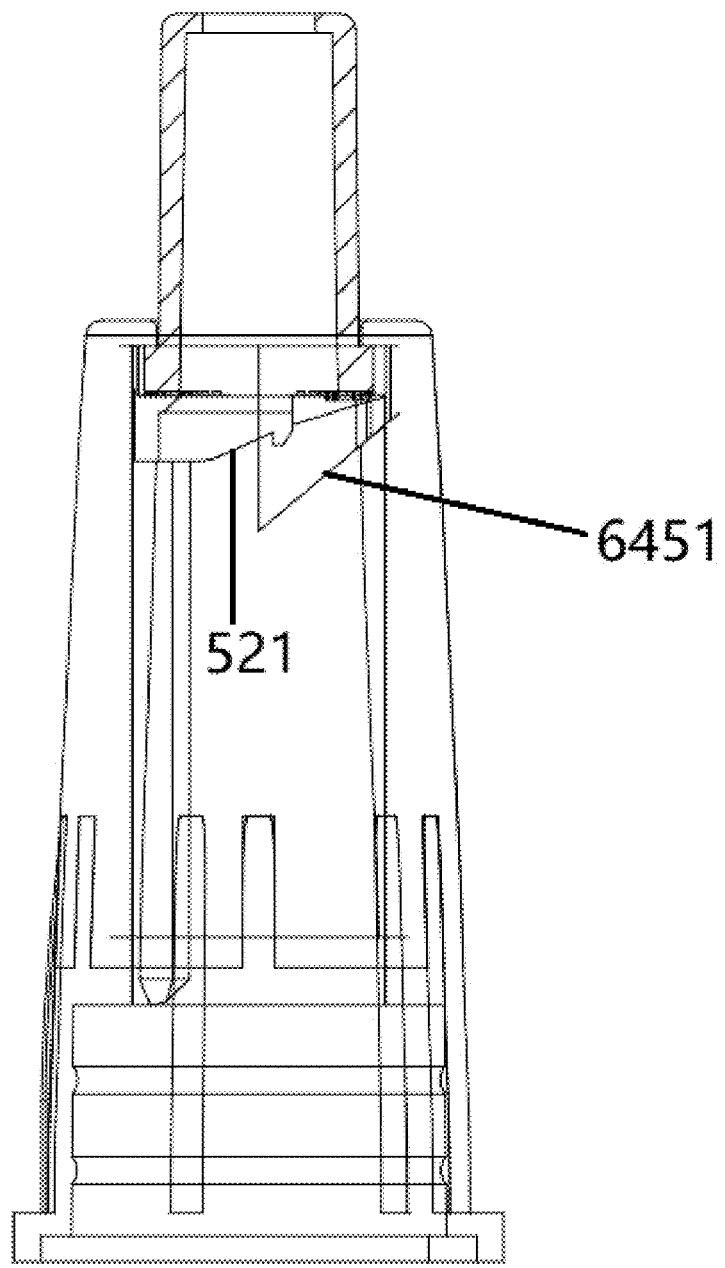
FIG. 21 is a schematic diagram of cooperation between a slider and a protective sleeve according to a preferred embodiment of the present application.

As shown in FIG. 7, the bottom 62 of the protective sleeve 6 is provided with a snap ring 621 and a notch 622 disposed symmetrically. The inner wall of the protective sleeve 6 is provided with a guide structure 64. The guide structure 64 includes four guide bars 641, 642, 643, and 644, and a guide block 645. The guide block 645 has a inclined surface 6451, and the inclined surface 6451 is in contact with the limiting protrusion 422 of the slider 4 (as shown in FIGS. 20 and 21). When the force on the distal end surface 51 of the needle shield 5 is removed, the slider 4 pushes the needle shield 5 under the restoring force of the spring 3. When the spring 3 returns to a certain point, the inclined surface 421 of the pressure receiving portion 42 is disengaged from the inclined surface 521. At the same time, the inclined surface 421 of the pressure receiving portion 42 is guided by the inclined surface 6451, and is released from the blocking portion 523 to continue to rotate. The limiting protrusion 422 of the slider 4 falls into the restricting area 522 and cannot return to the state of being in contact with the first inclined surface 521.

Figure 8:
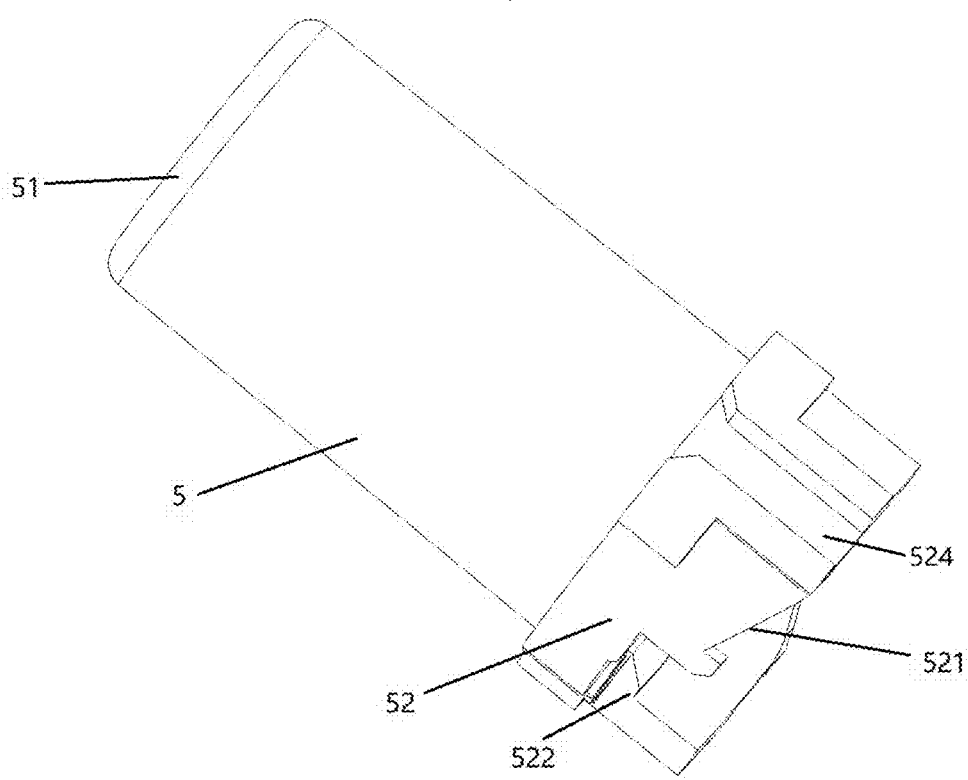
FIG. 8 is a schematic diagram of the outer structure of a needle shield according to a preferred embodiment of the present application.

As shown in FIG. 8, the proximal end surface 52 of the needle shield 5 has a groove 524. The groove 524 cooperates with the guide structure 64 of the protective sleeve 6 so that the needle shield 5 does not rotate relative to the protective sleeve 6.

Figure 9:
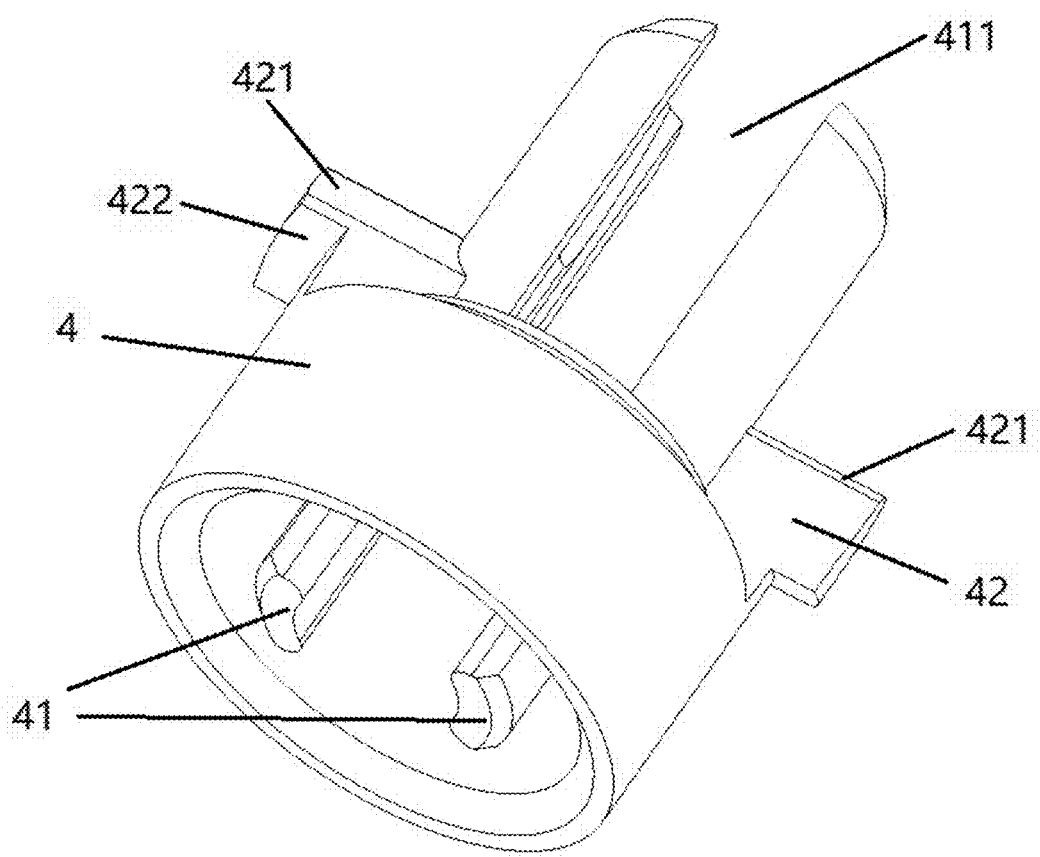
FIG. 9 is a schematic diagram of the structure of a slider according to a preferred embodiment of the present application.

As shown in FIG. 9, the guide portion 41 of the slider 4 has a through groove 411. The distal end of the spring 3 is sleeved on the proximal end of the guide portion 41.

Figure 11:
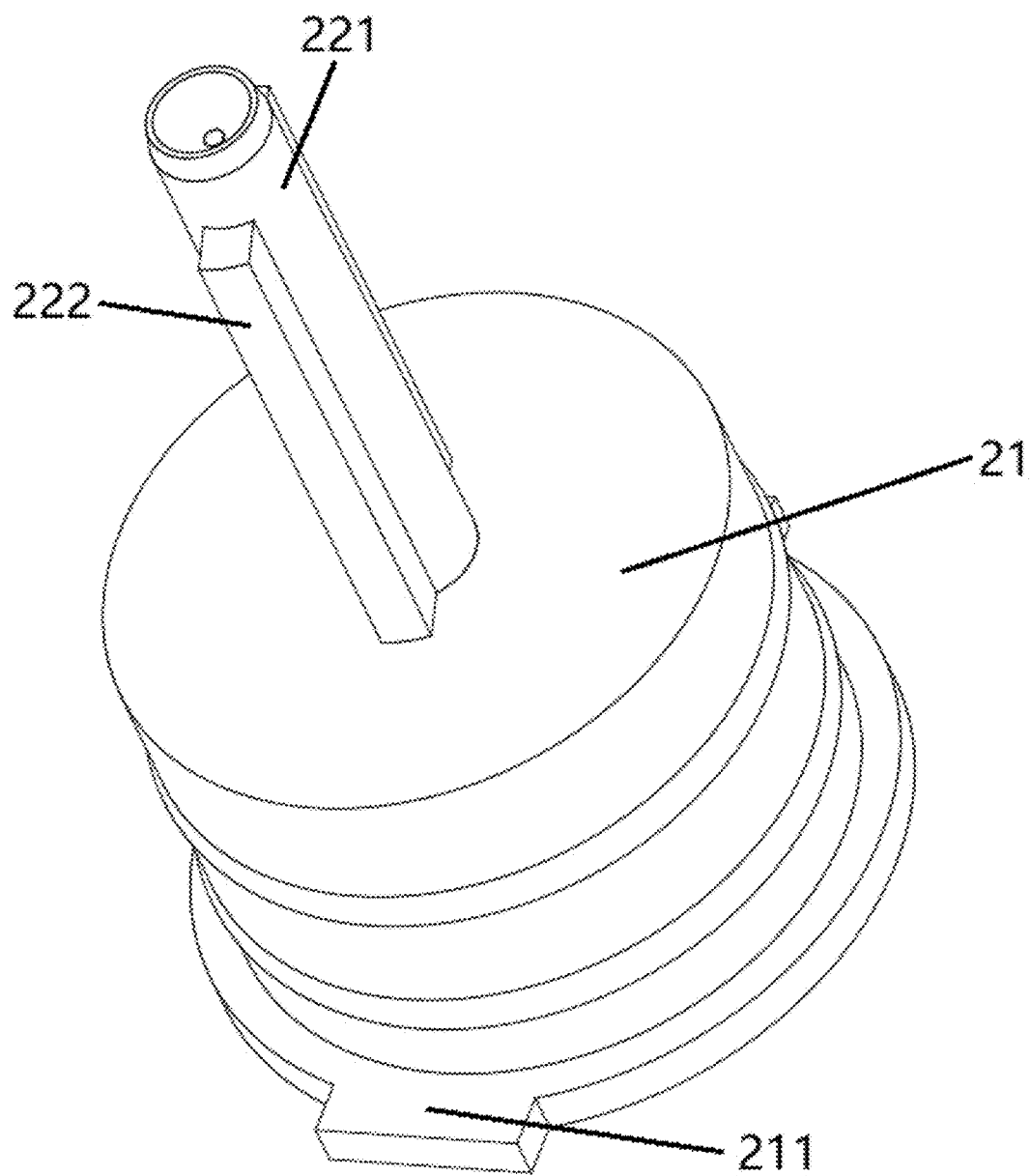
FIG. 11 is a schematic diagram of the structure of a needle hub according to a preferred embodiment of the present application.
Figure 12:
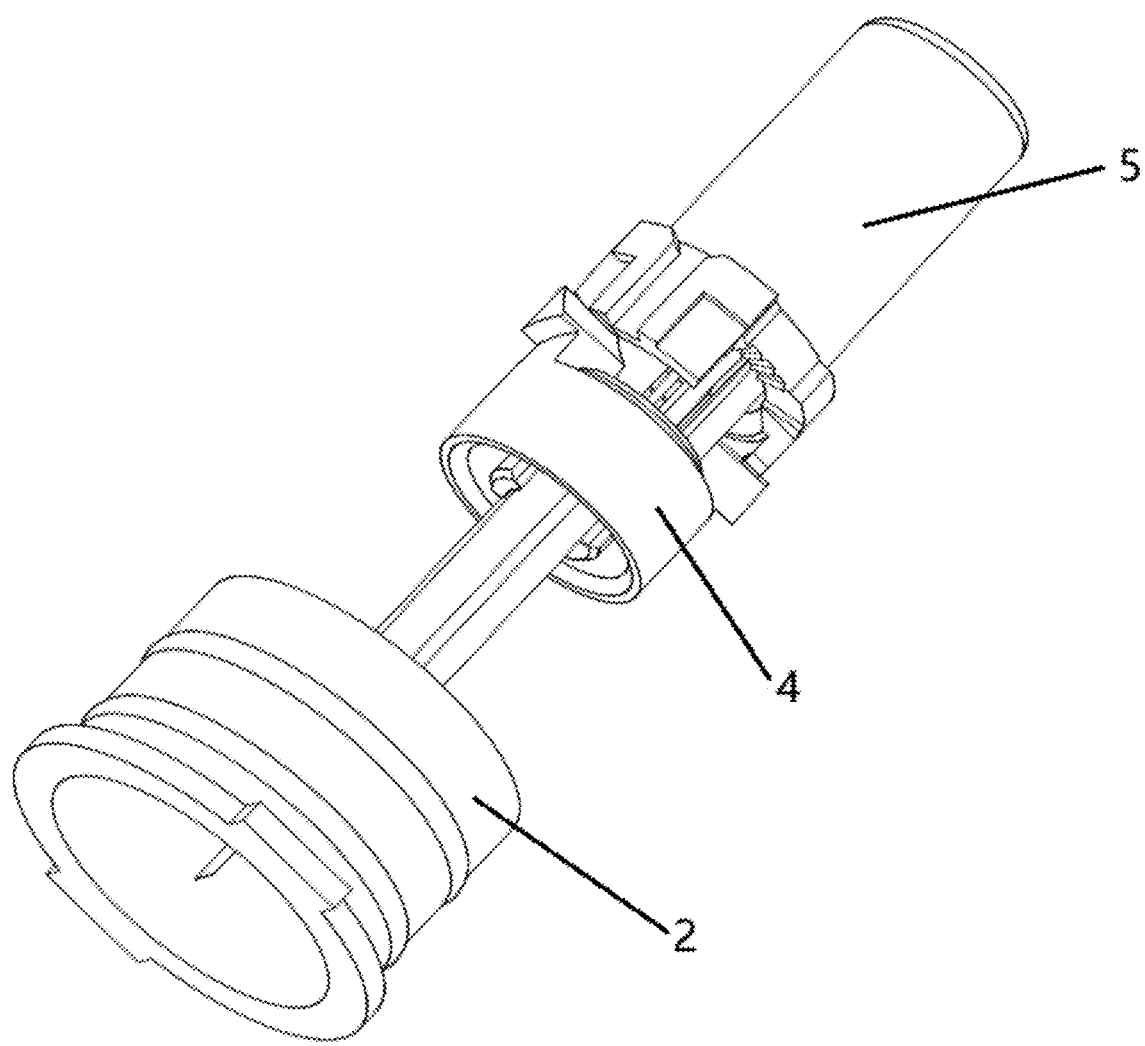
FIG. 12 is a diagram of an injection device in a compression injection state according to a preferred embodiment of the present application.
Figure 13:
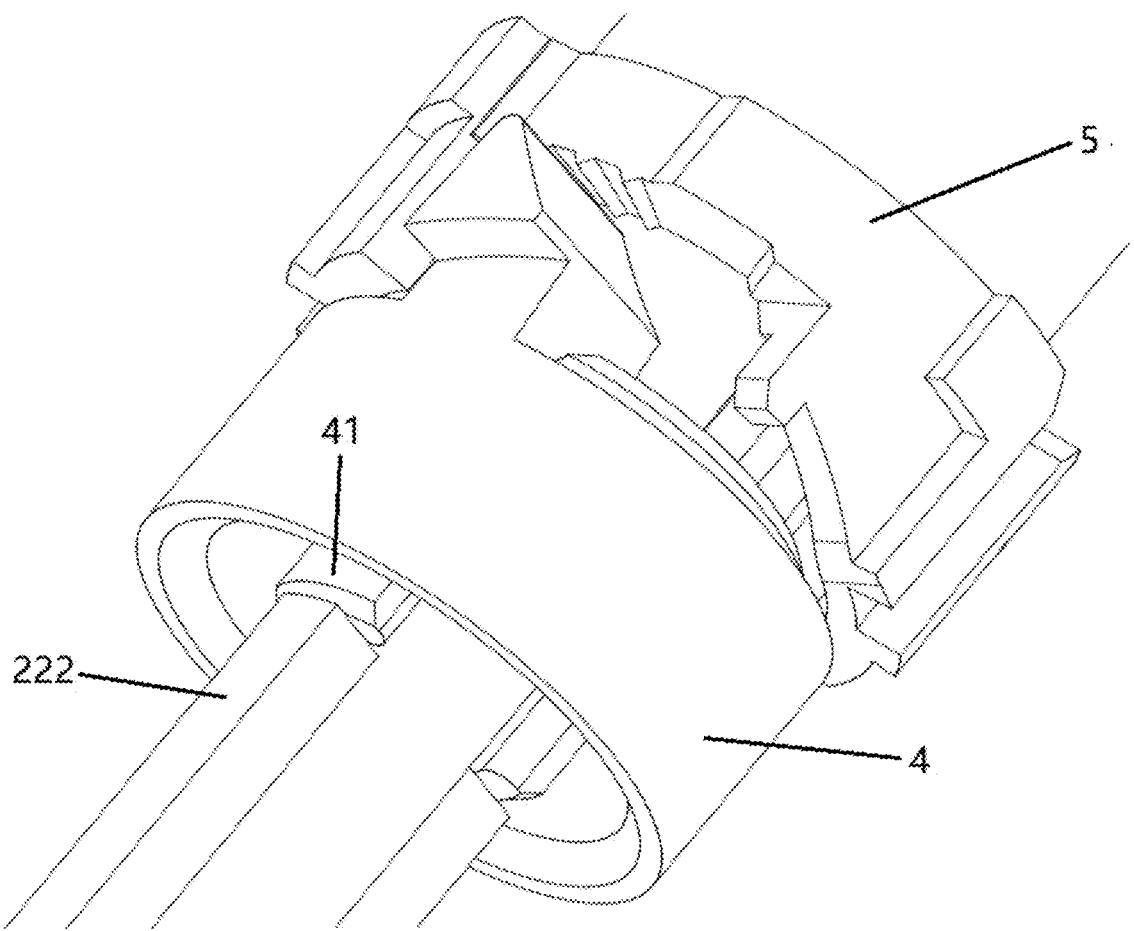
FIG. 13 is a schematic diagram of anti-reuse lock of an injection device according to a preferred embodiment of the present application.

As shown in FIG. 11, the needle hub 2 includes a base 21 and a rod 22. A lug 211 is provided on the base 21, and the lug 211 fits into the notch 622 of the protective sleeve 6. The rod 22 includes a rod core 221 and an extension portion 222. When the needle shield 5 is pressed for the first time, the extension portion 222 is inserted into the through groove 411 of the guide portion 41, so that the spring 3 is fully compressed (as shown in FIG. 12, the spring 3 is not shown). When the needle shield 5 is released, the slider 4 is irreversibly rotated, so that the extension portion 222 cannot fit into the through groove 411 of the guide portion 41 (as shown in FIG. 13). At this time, the spring 3 is not completely compressed, and the movement of the needle shield 5 is restricted, so that the distal end 11 of the needle 1 cannot extend out of the needle shield 5 again, and the purpose of preventing re-use is completely achieved.

Figure 14:
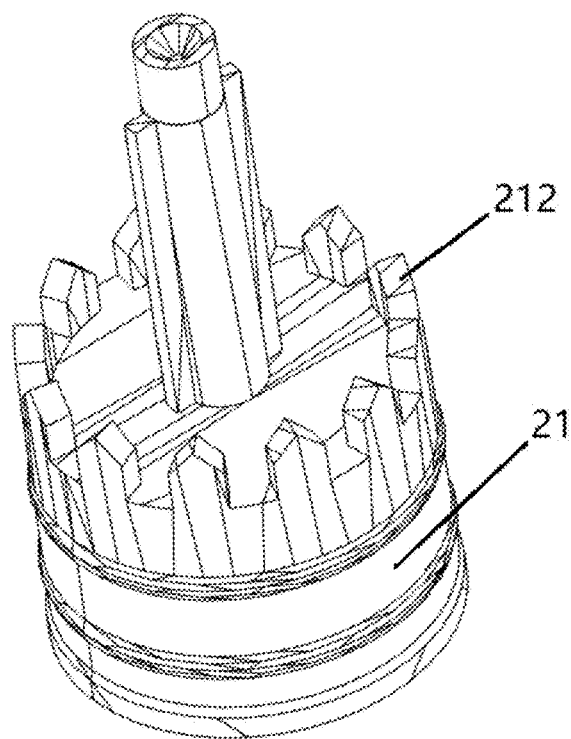
FIG. 14 is a schematic diagram of a needle hub according to another preferred embodiment of the present application.
Figure 15:
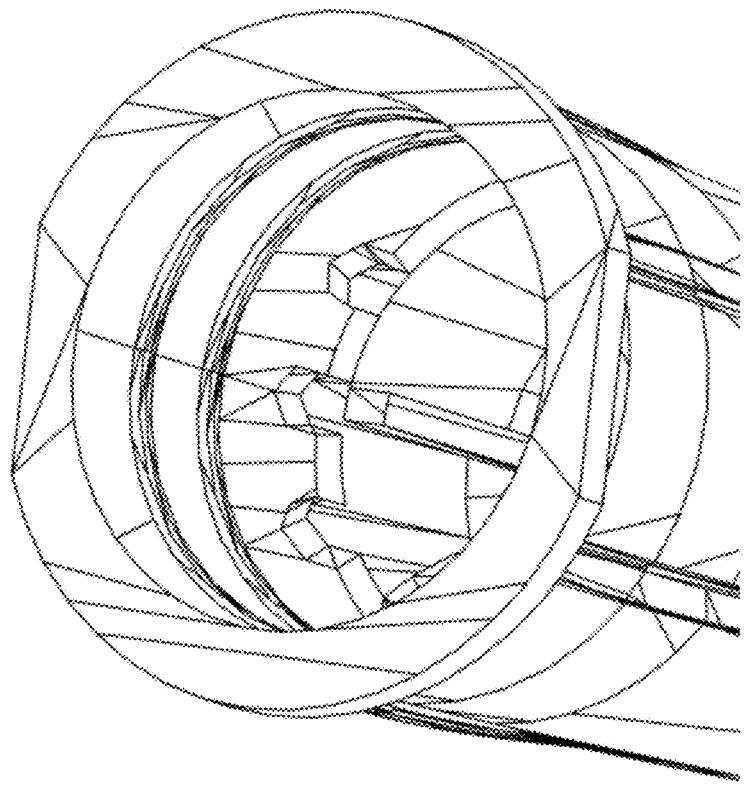
FIG. 15 is a schematic diagram of the internal structure of a protective sleeve according to another preferred embodiment of the present application.

FIGS. 14 and 15 show another preferred embodiment of the present application. The base 21 of the needle hub 2 is provided with convex teeth 212. A convex teeth structure corresponding to the convex teeth 212 is also provided on the inner side of the protective sleeve 6. When the base 21 with the convex teeth 212 is assembled with the protective sleeve 6, the relative positions of the base 21 and the protective sleeve 6 can be roughly defined, the function of which is the same as that of the lug 211 and the notch 622 of the protective sleeve 6 in the previous embodiment.

Figure 16:
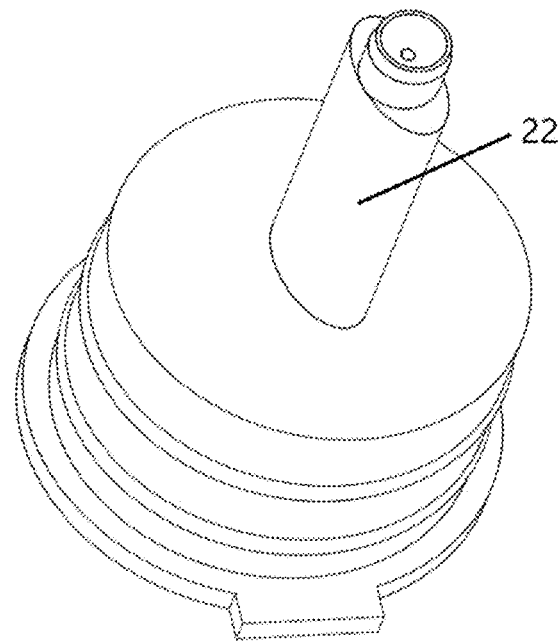
FIG. 16 is a schematic diagram of a needle hub according to another preferred embodiment of the present application.
Figure 17:
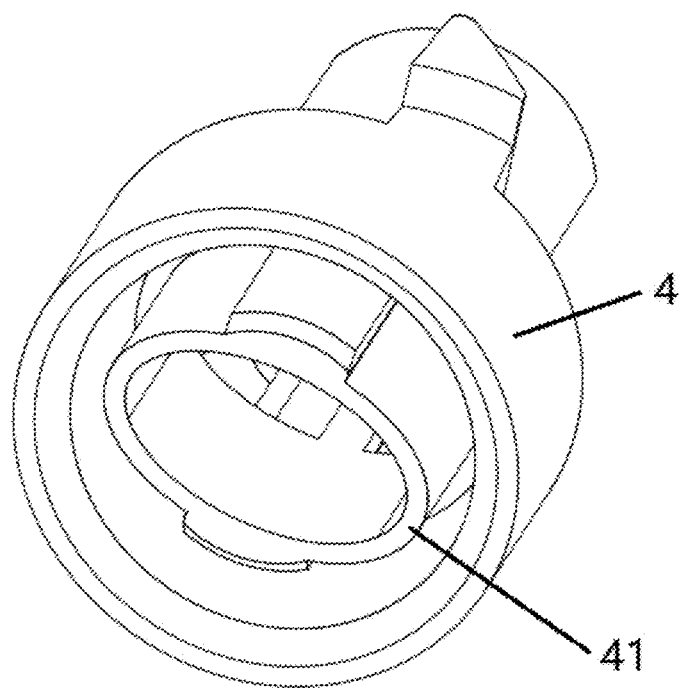
FIG. 17 is a schematic diagram of a slider according to another preferred embodiment of the present application.
Figure 18:
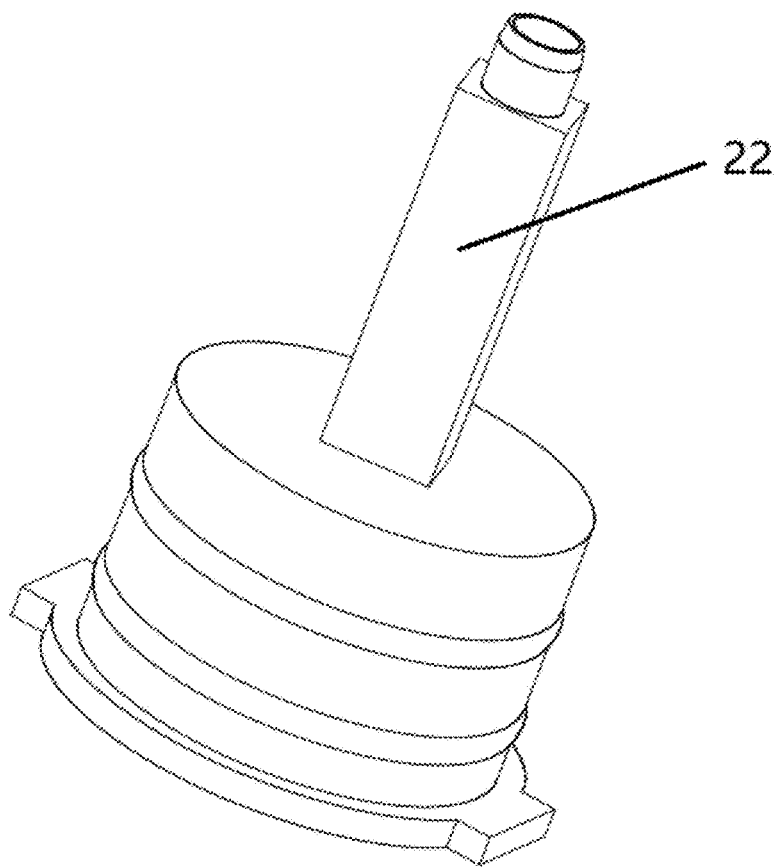
FIG. 18 is a schematic diagram of a needle hub according to another preferred embodiment of the present application.
Figure 19:
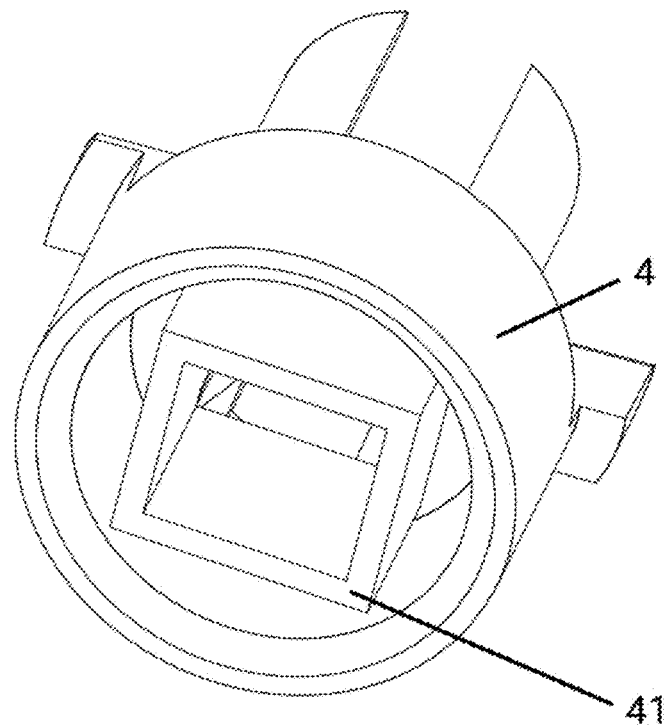
FIG. 19 is a schematic diagram of a slider according to another preferred embodiment of the present application.

FIGS. 16 and 17 show another preferred embodiment of the present application, wherein the rod 22 and the guide portion 41 are provided in an oval shape. FIGS. 18 and 19 show another preferred embodiment of the present application, wherein the rod 22 and the guide portion 41 are provided in a rectangular shape. It can be seen that, as long as the shapes of the rod 22 and the guide portion 41 can be fitted into each other and are not rotationally symmetrical, the object of the present application can be achieved.

Figure 10:
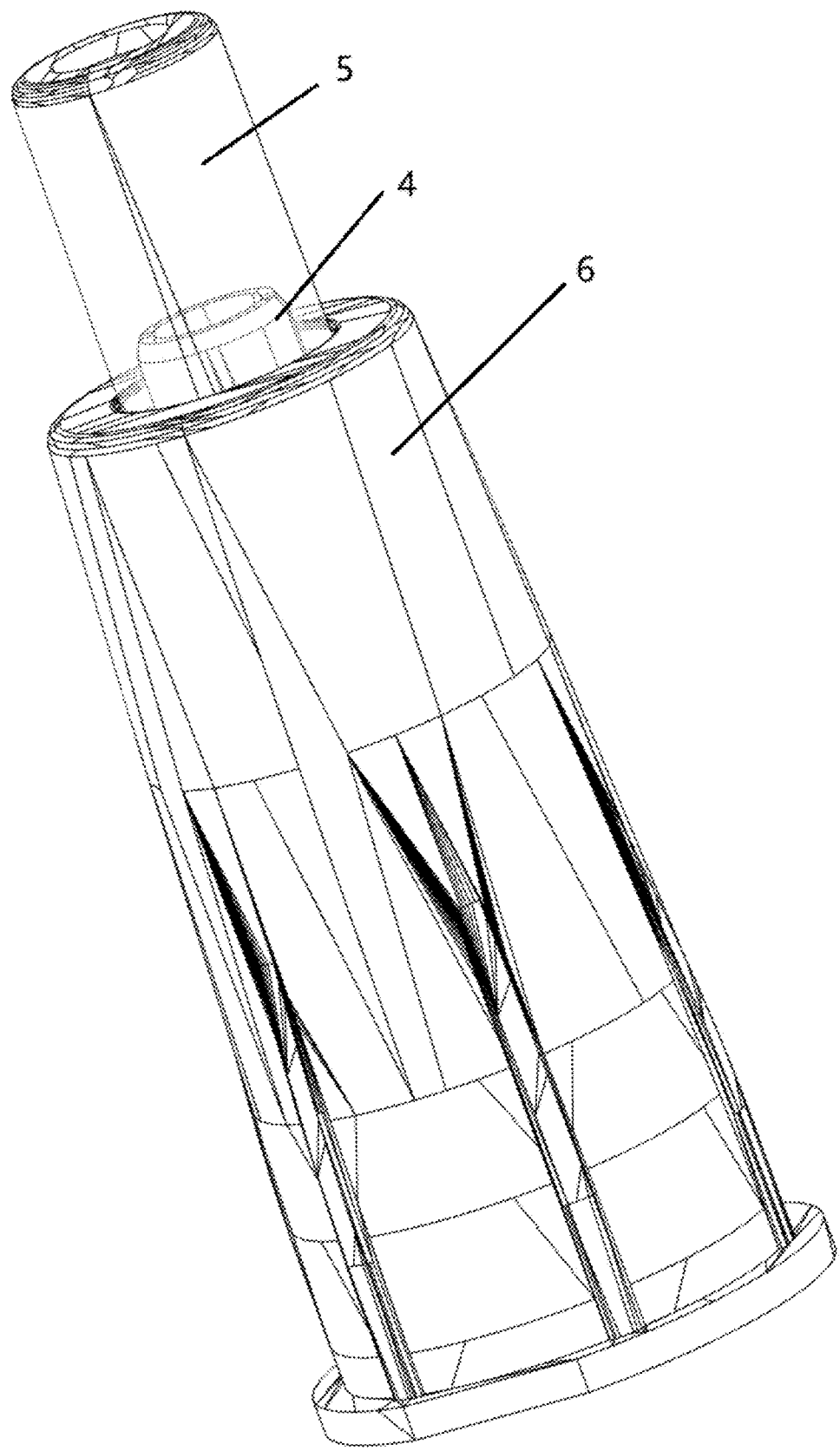
FIG. 10 is a schematic diagram of an injection device using an indicating color according to another preferred embodiment of the present application.

As shown in FIG. 10, in another preferred embodiment of the present application, the distal part or the whole of the slider 4 has an indicating color, which is used to indicate whether the injection device has been used. The indicating color is preferably red or yellow. In this embodiment, in the initial state, the slider 4 is restricted to the blocking portion 523 of the needle shield 5 after the initial rotation. After the injection is completed, under the action of the elastic force of the spring 3, the slider 4 crosses the blocking portion 523 and is under the guidance of the inclined surface 6451, and irreversible rotation occurs, resulting in the slider 4 protruding from the protective sleeve 6. Through the transparent needle shield 5, the indicating color of the slider 4 is displayed, thereby realizing visual display of different states before and after use.

The preferred embodiments of the present application have been described in detail above. It should be understood that many modifications and changes can be made to the concept of the present application without creative effort according to the ordinary technology in the art. Therefore, any technical solution based on the prior art that can be obtained by a person skilled in the art through logic analysis, reasoning, or limited experiments according to the concept of the present application should fall within the protection scope defined by the claims.

What is claimed is:

1. A safety injection device, comprising:
    a needle, with one end connecting to an injection as a proximal end and the other end as a distal end;
    a slider, being sleeved on the needle with the needle as a shaft;
    a needle shield, being sleeved on the needle with the needle as a shaft, and a proximal end of the needle shield being in contact with a distal end of the slider;
    a protective sleeve, being sleeved on the needle with the needle as a shaft, and an inner wall of the protective sleeve being in contact with an outer wall of the needle shield and an outer wall of the slider; and
    an elastic member, being sleeved on the needle with the needle as a shaft, and a distal end of the elastic member being in contact with a proximal end of the slider;
    wherein, the slider is configured to rotate irreversibly after a single use.

2. The safety injection device according to claim 1, wherein the proximal end surface of the needle shield has a first inclined surface; the slider has a pressure receiving portion being in contact with the first inclined surface of the needle shield; and when the needle shield moves toward the slider, the pressure receiving portion moves along the first inclined surface.

3. The safety injection device according to claim 2, wherein one end of the first inclined surface has a blocking portion, and when the pressure receiving portion comes into contact with the blocking portion, the slider stops rotating and the elastic member is compressed.

4. The safety injection device according to claim 3, wherein a guide structure is provided on the inner wall of the protective sleeve, the guide structure includes a guide block, the guide block has a third inclined surface; the outer wall of the slider has a limiting protrusion, and the limiting protrusion is in contact with the third inclined surface; when the needle shield continues to move toward the slider, the elastic member continues to compress, and the limiting protrusion moves under the guidance of the third inclined surface; the pressure receiving portion crosses the blocking portion and disengages from the first inclined surface; the slider continues to rotate, and the pressure receiving portion falls into the restricting area of the needle shield.

5. The safety injection device according to claim 4, wherein the guide structure further includes a guide bar, the outer wall of the proximal end of the needle shield has a groove, and the groove cooperates with the guide bar to prevent relative rotation between the needle shield and the protective sleeve with the needle as a shaft.

6. The safety injection device according to claim 5, wherein the slider cannot return to an initial position after the elastic force of the elastic member is completely released since the pressure receiving portion falls into the restricting area of the needle shield.

7. The safety injection device according to claim 6, wherein the safety injection device further comprises a needle hub which is sleeved on the needle with the needle as a shaft, and a proximal end of the needle hub is in contact with the proximal end of the protective sleeve; the needle hub includes a base and a rod, and the rod includes a rod core and an extension portion; wherein the proximal end of the slider has a through hole; when the pressure receiving portion enters the restricting area of the needle shield, the shapes of the extension portion and the through hole do not match and interfere, the movement of the needle shield towards the slider no longer causes deformation of the elastic member.

8. The safety injection device according to claim 7, wherein the cross-sectional shape of the extension portion is rectangular or oval.

9. The safety injection device according to claim 7, wherein an outside wall of the proximal end of the needle hub is provided with a lug or threads or concave-convex teeth, and an outside wall of the proximal end of the protective sleeve is correspondingly provided with a groove or threads or concave-convex teeth.

10. The safety injection device according to claim 1, wherein the distal end of the needle shield is provided with a first hole, through which the distal end of the needle protrudes from the needle shield to contact an injection site.

11. The safety injection device according to claim 1, wherein the distal end of the protective sleeve is provided with a second hole and the needle shield passes through the second hole for axial reciprocating motion with the needle as a shaft.

12. The safety injection device according to claim 1, wherein the outside wall of the protective sleeve is provided with a reinforcing rib with an inclined surface and the reinforcing rib extends to the proximal end of the protective sleeve.

13. The safety injection device according to claim 1, wherein the slider has a different color from other components, and the needle shield sleeved outside the slider is made of transparent material.

14. An injector comprising the safety injection device according to claim 1.

* * * * *